(12) United States Patent
Simmons et al.

(10) Patent No.: US 7,749,181 B2
(45) Date of Patent: *Jul. 6, 2010

(54) PATELLOFEMORAL BRACE

(75) Inventors: Richard Royle Simmons, San Marcos, CA (US); John P. Fulkerson, Litchfield, CT (US); John Patrick Martin, Oceanside, CA (US); Andy Kazmierczak, Oceanside, CA (US)

(73) Assignee: DJO, LLC, Vista, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 11/495,488

(22) Filed: Jul. 28, 2006

(65) Prior Publication Data

US 2006/0264793 A1 Nov. 23, 2006

Related U.S. Application Data

(63) Continuation of application No. 10/357,523, filed on Feb. 3, 2003, now Pat. No. 7,083,586.

(51) Int. Cl.
*A61F 5/00* (2006.01)
(52) U.S. Cl. .............................. 602/23; 602/26; 128/882
(58) Field of Classification Search .................... 602/5, 602/16, 26, 60, 62, 63; 128/882
See application file for complete search history.

(56) References Cited

U.S. PATENT DOCUMENTS

| | | | |
|---|---|---|---|
| 3,473,527 A | 10/1969 | Spiro | |
| 3,581,741 A | 6/1971 | Rosman et al. | |
| 3,786,804 A | 1/1974 | Lewis | |
| 3,804,084 A | 4/1974 | Lehman | |
| 3,817,244 A | 6/1974 | Taylor | |
| 3,945,046 A | 3/1976 | Stromgren | |
| 4,064,874 A | 12/1977 | Valin | |
| 4,116,236 A | 9/1978 | Albert | |
| 4,201,203 A | 5/1980 | Applegate | |
| 4,287,884 A | 9/1981 | Applegate | |
| 4,287,885 A | 9/1981 | Applegate | |
| 4,296,744 A | 10/1981 | Palumbo | |
| 4,353,362 A | 10/1982 | DeMarco | |
| 4,366,813 A | 1/1983 | Nelson | |
| 4,370,978 A | 2/1983 | Palumbo | |

(Continued)

FOREIGN PATENT DOCUMENTS

DE 1024204 2/1958

(Continued)

*Primary Examiner*—Michael A. Brown
(74) *Attorney, Agent, or Firm*—Ropes & Gray LLP (57) ABSTRACT

A patellofemoral brace including a buttress for supporting a wearer's patella is provided. The patellofemoral brace includes an elastic sleeve that is easy to apply to the wearer's leg and easy to remove from the wearer's leg. The sleeve includes distinct bands of material so that end bands are substantially rotationally independent of a central band. The end bands resist translation along and rotation about the wearer's leg. The brace further includes a tensioning strap that lies across the buttress to further support the buttress and the wearer's patella. A portion of the tensioning strap is constructed of a thermoplastic elastomer, so that the strap provides firmer support to the buttress than a fabric strap, but is more comfortable and more evenly supports the buttress than a hard, inelastic strap.

14 Claims, 10 Drawing Sheets

U.S. PATENT DOCUMENTS

| | | | |
|---|---|---|---|
| 4,378,009 A | 3/1983 | Rowley et al. | |
| 4,445,505 A | 5/1984 | Labour et al. | |
| 4,651,722 A | 3/1987 | Karczewski | |
| 4,697,583 A | 10/1987 | Mason et al. | |
| 4,700,698 A | 10/1987 | Kleylein | |
| 4,872,448 A | 10/1989 | Johnson, Jr. | |
| 4,887,590 A | 12/1989 | Logue et al. | |
| 4,938,207 A | 7/1990 | Vargo | |
| 4,941,462 A | 7/1990 | Lindberg | |
| 4,986,263 A | 1/1991 | Dickerson et al. | |
| 5,016,621 A | 5/1991 | Bender | |
| 5,024,216 A | 6/1991 | Shiono | |
| 5,036,837 A | 8/1991 | Mitchell et al. | |
| 5,139,476 A | 8/1992 | Peters | |
| 5,139,477 A | 8/1992 | Peters | |
| 5,221,252 A | 6/1993 | Caprio, Jr. et al. | |
| 5,261,871 A | 11/1993 | Greenfield | |
| 5,267,951 A | 12/1993 | Ishii | |
| 5,277,697 A * | 1/1994 | France et al. | 602/16 |
| 5,334,135 A | 8/1994 | Grim et al. | |
| 5,383,843 A | 1/1995 | Watson et al. | |
| 5,385,538 A | 1/1995 | Mann | |
| 5,399,153 A * | 3/1995 | Caprio et al. | 602/26 |
| 5,411,037 A | 5/1995 | Hess et al. | |
| 5,417,646 A | 5/1995 | Gauvry | |
| 5,419,161 A | 5/1995 | Bodenschatz et al. | |
| 5,451,201 A | 9/1995 | Prengler | |
| 5,462,517 A | 10/1995 | Mann | |
| 5,472,413 A | 12/1995 | Detty | |
| 5,512,039 A | 4/1996 | White | |
| 5,527,267 A | 6/1996 | Billotti | |
| 5,554,105 A | 9/1996 | Taylor | |
| 5,599,288 A | 2/1997 | Shirley et al. | |
| 5,626,557 A | 5/1997 | Mann | |
| 5,695,452 A | 12/1997 | Grim et al. | |
| 5,711,312 A | 1/1998 | Staudinger | |
| 5,759,167 A * | 6/1998 | Shields et al. | 602/26 |
| 5,792,084 A | 8/1998 | Wilson et al. | |
| 5,797,864 A | 8/1998 | Taylor | |
| 5,807,298 A | 9/1998 | Palumbo | |
| 5,873,848 A * | 2/1999 | Fulkerson | 602/62 |
| 6,238,360 B1 | 5/2001 | Gildersleeve et al. | |
| 6,287,269 B1 * | 9/2001 | Osti et al. | 602/62 |
| 6,336,909 B2 | 1/2002 | Gildersleeve et al. | |
| 6,551,267 B1 | 4/2003 | Cohen et al. | |
| 7,004,919 B2 * | 2/2006 | Gaylord et al. | 602/62 |
| 7,083,586 B2 * | 8/2006 | Simmons et al. | 602/23 |
| 2004/0054307 A1 | 3/2004 | Mason et al. | |
| 2004/0153017 A1 | 8/2004 | Simmons et al. | |

FOREIGN PATENT DOCUMENTS

| | | |
|---|---|---|
| DE | 27 24 586 A1 | 12/1978 |
| DE | 35 11 250 A1 | 7/1985 |
| DE | 4013693 | 8/1991 |
| EP | 0 290 409 A1 | 11/1988 |
| EP | 0 809 478 B1 | 12/1997 |
| FR | 2486388 | 1/1982 |
| FR | 2807644 | 10/2001 |
| GB | 2136294 A | 9/1984 |
| JP | 2001-070329 | 3/2001 |
| WO | WO 00/51537 | 9/2000 |

* cited by examiner

PATELLOFEMORAL BRACE

CROSS-REFERENCE TO RELATED APPLICATIONS

This application is a continuation of application Ser. No. 10/357,523, filed on Feb. 3, 2003, now U.S. Pat. No. 7,083,586, the entire contents of which are hereby incorporated by reference.

BACKGROUND OF THE INVENTION

1. Field of the Invention

The present invention relates to orthopedic braces. More particularly, the present patellofemoral brace provides a soft sleeve that can be worn about the knee to help prevent patellar subluxation and provide relief from other knee ailments.

2. Description of the Related Art

Many orthopedic braces are capable of supporting the human patella. For example, U.S. Pat. No. 4,296,744 to Palumbo discloses a dynamic patellar brace for both diagnosis and treatment of patellar subluxation. The brace includes a patellar bracing pad adapted to be positioned laterally with respect to the patella. The pad applies medial pressure to the patella to help prevent subluxation. Straps secure the brace about the wearer's leg. The straps wrap around the wearer's leg and are then secured to the same portion of the brace from which they originate. Thus, although this brace is intended to apply pressure to one side of the patella, the manner in which the straps are secured to the brace actually creates a force on the brace in the opposite direction. This unintended force reduces the effectiveness of the brace.

dj Orthopedics, LLC of Vista, Calif. markets several different knee braces for treating patellar subluxation. Generally, each of these braces includes an elastic sleeve that fits snugly over the wearer's knee. The sleeve is constructed of one continuous length of elastic material. The wearer's patella protrudes slightly from an aperture on an anterior portion of the sleeve. A dense buttress surrounds at least a portion of the aperture and supports the patella. The buttress may be shaped as a donut, a C, a J, an H, or any other appropriate shape. A fabric strap may be secured to one side of the brace. The strap stretches across the aperture and is secured to the brace on the opposite side. The strap applies pressure to the buttress, further reinforcing the support provided to the patella by the buttress. However, the strap is securable to the sleeve, which is one continuous length of elastic material. Thus, tension in the strap tends to twist the sleeve in a direction that removes pressure from the buttress.

A brace manufactured by Breg, Inc. of Vista, Calif. includes an elastic sleeve that fits snugly over the wearer's knee. The wearer's patella protrudes slightly from an aperture on an anterior portion of the sleeve. A crescent shaped buttress borders the aperture and supports the patella. An inelastic, hard, plastic, crescent shaped reinforcing member is secured to the sleeve adjacent the buttress and overlies the buttress. Ends of the reinforcing member include apertures that accept straps. The straps extend from a side portion of the brace opposite the buttress. The straps thread through the apertures at the ends of the reinforcing member, and then fold back over themselves. Hook-and-loop fastener secures the free ends of the straps to themselves. When the brace wearer pulls the straps taut, the reinforcing member exerts a supporting force on the buttress. However, because the reinforcing member is constructed of an inelastic and hard plastic, the reinforcing member does not yield in response to the wearer's movements. Therefore, the reinforcing member does not provide even pressure to all portions of the buttress. Furthermore, the reinforcing member can make the brace somewhat uncomfortable to wear.

U.S. Pat. No. 5,873,848 to Fulkerson discloses an orthopedic brace including a first strap, a second strap, and a support member. The first strap is covered on one side with loop material from a hook and loop-type fastener. A section of hook material is secured to the opposite side of the first strap. Similarly, the second strap has loop material secured to one side thereof, and a hook portion secured to the opposite side. The second strap is shorter than the first strap. The support member includes a body segment with a support pad removably secured thereto. A pair of support straps extend from the body. One side of each support strap includes both loop material and a segment of hook material secured thereto. The side of the body opposite the hook and loop material of the support straps is likewise covered with loop material and includes two hook material portions. In use, the first strap is wrapped around one portion of the limb above a joint and the second strap is wrapped around another portion of the limb below the joint. The support member is then wrapped around the limb such that the support pad is disposed adjacent the joint and one support strap is secured to the first strap above the joint and the other support strap is secured to the second strap below the joint.

The brace of Fulkerson is cumbersome to secure about one's knee. The brace includes three separate pieces that are each secured to the wearer's leg individually. The wearer first secures straps 10, 20 to his or her leg above and below the knee, respectively. The wearer then positions the support member 30 against his or her knee and, while holding the support member in place with one hand, wraps the support straps 50 around his or her leg with his or her other hand, engaging the loop material on the second surfaces 54 with the hook material 43 on the body 40. Finally, the wearer further wraps the support straps spirally around his or her leg such that one hook portion 57 engages the loop material on the second surface 15 of first strap 10, and the other hook portion 57 engages the loop material on the second surface 25 of the second strap 20. This process is time consuming and requires a great deal of coordination and practice to achieve the desired results. Therefore, a knee brace that provided the advantages of Fulkerson, but was easier to secure about one's knee, would be of great benefit to people who suffer from patellofemoral subluxation and other knee ailments.

SUMMARY OF THE INVENTION

The preferred embodiments of the present patellofemoral brace have several features, no single one of which is solely responsible for their desirable attributes. Without limiting the scope of this patellofemoral brace as expressed by the claims that follow, its more prominent features will now be discussed briefly. After considering this discussion, and particularly after reading the section entitled "Detailed Description of the Preferred Embodiments," one will understand how the features of the preferred embodiments provide advantages, which include the ability to maintain adequate and consistent tension in a tensioning strap that supports a patellar supporting buttress, firmer support for the buttress due to the use of firmer materials, and ease of application and removal of the brace from the wearer's leg.

A preferred embodiment of the present patellofemoral brace comprises a substantially cylindrical sleeve subdivided into substantially cylindrical bands. The bands include a knee encircling band, a proximal spacer band secured to a proximal edge of the knee encircling band, a distal spacer band secured to a distal edge of the knee encircling band, a proximal anchor band secured to a proximal edge of the proximal spacer band, and a distal anchor band secured to a distal edge of the distal spacer band.

A preferred embodiment of the present patellofemoral brace comprises a sleeve adapted to encircle a wearer's knee. The sleeve includes a buttress on an anterior portion thereof. A tensioning strap having a free end is secured at a first end to the sleeve adjacent the buttress. At least a portion of the tensioning strap is constructed of a thermoplastic elastomer, and the thermoplastic elastomer lies across and applies pressure to the buttress when the free end of the strap is extended across the buttress and secured to the sleeve.

BRIEF DESCRIPTION OF THE DRAWINGS

The preferred embodiments of the present patellofemoral brace, illustrating its features, will now be discussed in detail. These embodiments depict the novel and non-obvious patellofemoral brace shown in the accompanying drawings, which are for illustrative purposes only. These drawings include the following figures, in which like numerals indicate like parts.

DETAILED DESCRIPTION OF THE PREFERRED EMBODIMENTS

FIGS. 1-6 illustrate a preferred embodiment of the present patellofemoral brace 10, and FIGS. 7-10 illustrate another preferred embodiment of the present patellofemoral brace 100. The patellofemoral brace 10 controls patellar subluxation/dislocation during knee extension, and relieves pain by controlling patellar mal tracking. The brace 10 also provides relief from patellar tendonitis, and relief from general anterior knee pain. For ease of reference, the present brace 10 will be described with reference to a wearer who is suffering from lateral subluxation of the left patella. Thus, the wearer would wear the brace 10 on his or her left leg. Those of skill in the art will appreciate that the illustrated brace 10 could also be worn on the right leg to treat medial subluxation of the right patella.

Those of skill in the art will further appreciate that the brace 10 could be inverted and worn on the left leg to treat medial subluxation of the left patella, or inverted and worn on the right leg to treat lateral subluxation of the right patella. Therefore, any directional terminology should not be interpreted as limiting.

Figure 2:
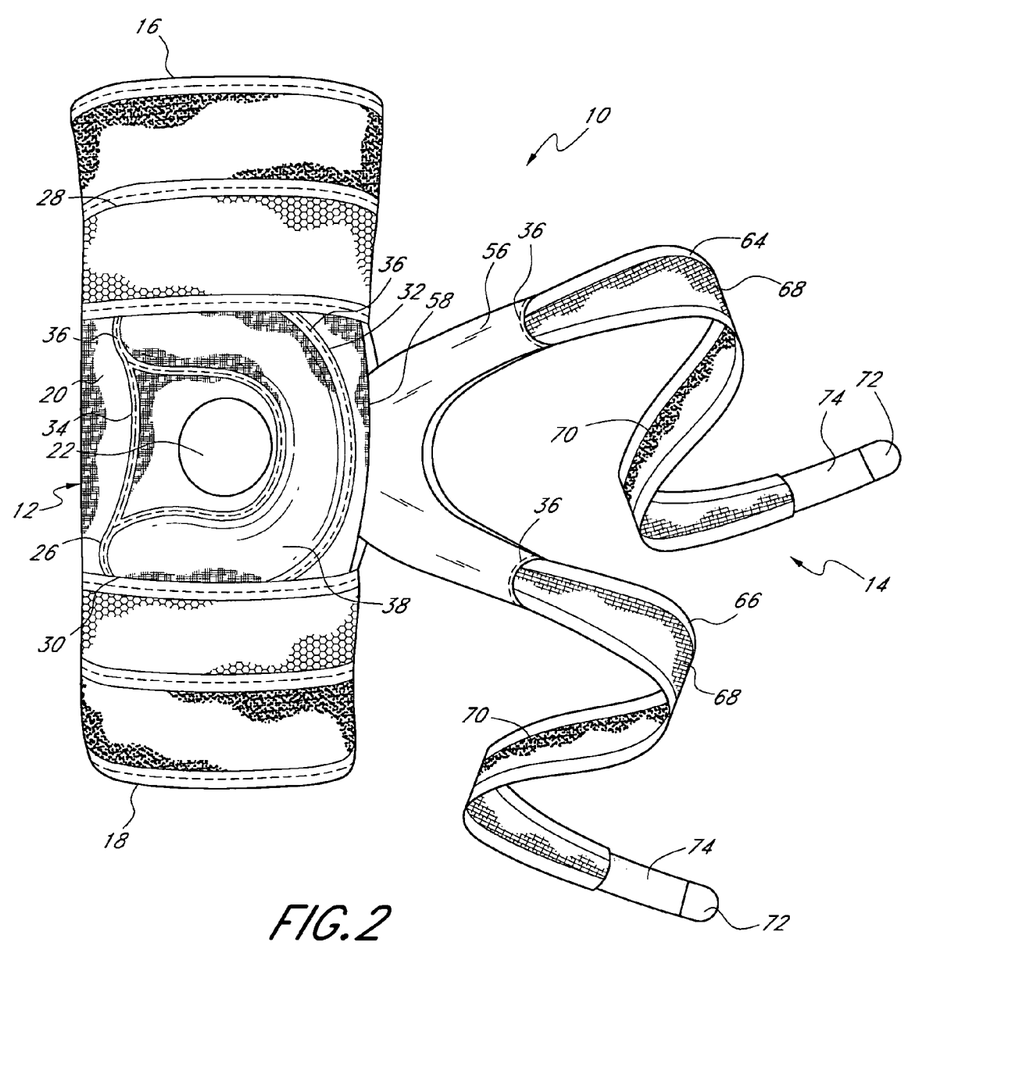
FIG. 2 is a front elevational view of the patellofemoral brace of FIG. 1, illustrating the tensioning strap released from the sleeve.

The brace 10 comprises a leg encircling sleeve 12 with an attached tensioning strap 14 (FIG. 2). From a proximal, or top, end 16 to a distal, or bottom, end 18, the sleeve preferably becomes progressively narrower to match the natural taper of the human leg. Also from the proximal end 16 to the distal end 18 the sleeve 12 includes distinct bands that may be constructed of different materials. A central band 20, adapted to encircle the wearer's knee, is preferably constructed of a flexible and stretchable material that is preferably lightweight, such as neoprene, or a knit fabric, or a breathable and stretchable mesh fabric. The central band 20 includes an anterior opening 22 at an anterior portion thereof, and a posterior opening 24 (FIG. 5) at a posterior portion thereof. The anterior opening 22 is adapted to encircle the patella of the wearer. The posterior opening 24 provides ventilation for the wearer and reduces the bulk of the brace 10, enabling the wearer to more easily flex his or her knee without pinching material. Those of skill in the art will appreciate that neither the anterior opening 22 nor the posterior opening 24 is necessary to achieve the advantages of the present brace 10.

The anterior portion of the central band 20 includes an irregularly shaped panel 26 (FIG. 2). The panel 26 includes a proximal edge 28 and a distal edge 30 that are each substantially straight. A convex arcuate lateral edge 32 connects lateral ends of the proximal and distal edges 28, 30 to one another, and a concave arcuate medial edge 34 connects medial ends of the proximal and distal edges 28, 30 to one another. The panel edges 28, 30, 32, 34 are preferably secured to the anterior portion of the central band 20 with stitching 36.

The panel 26 contains a substantially C-shaped buttress 38 that is adapted to support the wearer's patella, as described below. The buttress 38 is constructed of a dense but flexible material, such as foam, neoprene, felt, ethyl-vinyl acetate, or Poron®. The buttress 38 is shaped substantially as a cylinder that is bent along its longitudinal axis to form a C. The buttress 38 is preferably secured within a C-shaped pocket in the panel 26 with stitching 36. The pocket may include an opening (not shown) so that the buttress 38 may be easily removed and replaced with a different buttress, such as a buttress having a different thickness.

Straight legs of the C lie along the panel's proximal and distal edges 28, 30, and a curved base of the C lies along the panel's lateral edge 32. Those of skill in the art will appreciate that the buttress 38 could embody any of a number of shapes besides a C. For example, the buttress 38 may be shaped like a donut, or a J, or any other suitable shape to meet the needs of the wearer.

When the brace 10 is worn on the left leg in the orientation shown (FIG. 2), the buttress 38 abuts the proximal, lateral and distal edges of the wearer's left patella. The elasticity of the central band 20 material keeps the buttress 38 in adjacent contact with the patella. Thus, as the wearer straightens his or her knee, the buttress 38 prevents the patella from subluxing laterally. To prevent the left patella from subluxing medially, either the orientation of the buttress 38 relative to the central band 20 could be reversed, or a donut shaped buttress could be provided.

Figure 1:
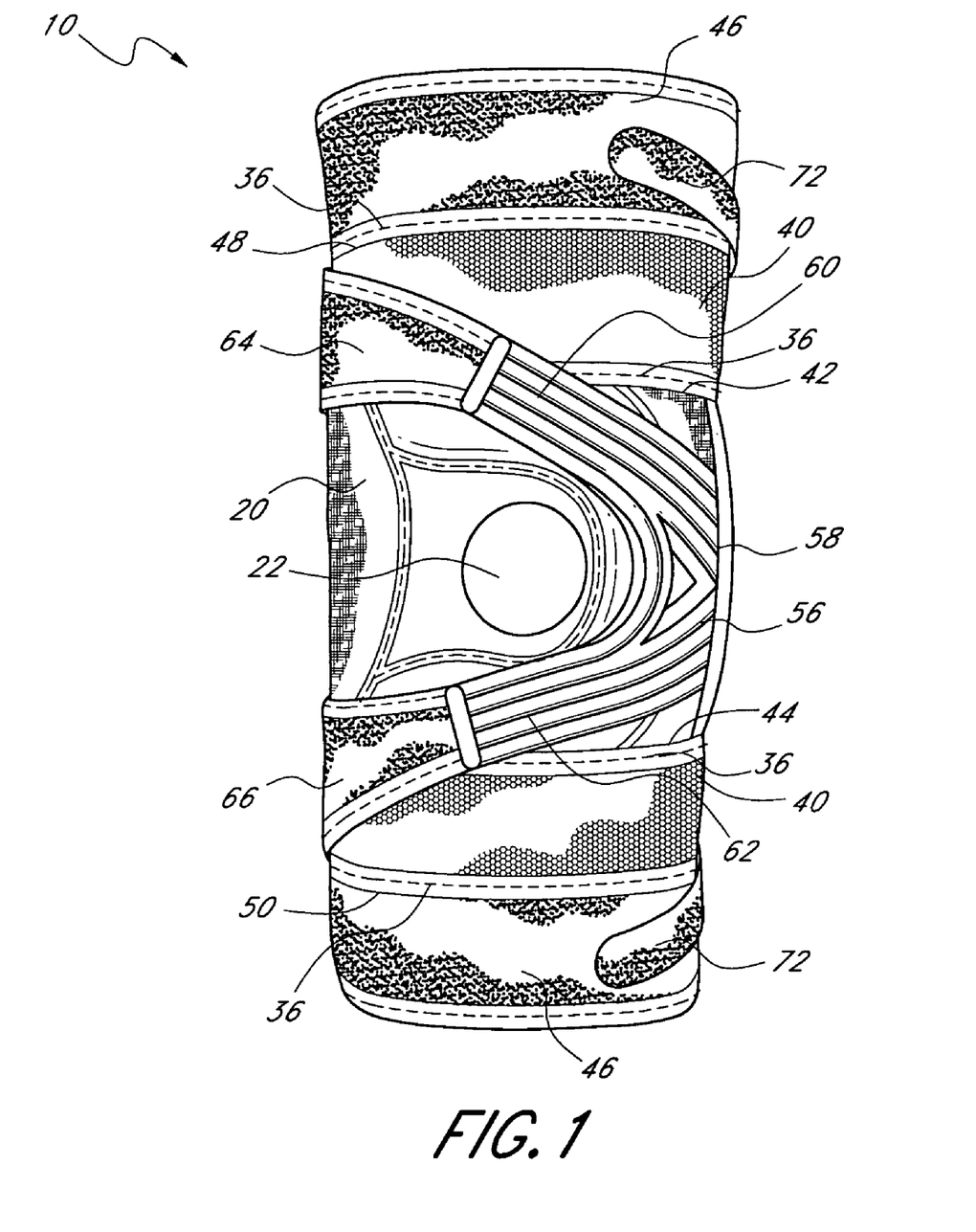
FIG. 1 is a front elevational view of a preferred embodiment of the present patellofemoral brace, illustrating the tensioning strap of the patellofemoral brace secured about the sleeve.

A proximal spacer band 40 is secured to a proximal edge 42 of the central band 20, and a distal spacer band 40 is secured to a distal edge 44 of the central band 20 (FIG. 1). Each spacer band 40 comprises a flat strip of material whose ends are secured together to form, substantially, a cylinder. Preferably, stitching 36 secures the ends of each spacer band 40 to one another (FIG. 5), and stitching 36 preferably secures the edges of the spacer bands 40 to the edges 42, 44 of the central band 20. The spacer bands 40 are preferably constructed of a breathable and stretchable mesh fabric.

A proximal anchor band 46 is secured to a proximal edge 48 of the proximal spacer band 40, and a distal anchor band 46 is secured to a distal edge 50 of the distal spacer band 40 (FIG. 1). Each anchor band 46 comprises a flat strip of material whose ends are secured together to form, substantially, a cylinder. Preferably, stitching 36 secures the ends of each anchor band 46 to one another (FIG. 5), and stitching 36 preferably secures the edges of the anchor bands 46 to the edges 48, 50 of the spacer bands 40. The anchor bands 46 are preferably constructed of a flexible and stretchable material that provides a large amount of grip when in contact with human skin. Preferred materials for the anchor bands 46 include neoprene and elastic materials that are silk-screened on an inside surface with high friction silicone dots.

Both anchor bands 46 are rotatable a small amount about the longitudinal axis of the brace 10. A partial rotation of either anchor band 46 relative to the central band 20 preferably will not significantly influence the central band 20. For example, if the central band 20 is held fixed, and the proximal anchor band 46 is rotated about the longitudinal axis relative to the central band 20, the proximal spacer band 40 will coil slightly. Because of the flexibility and stretchability of the proximal spacer band 40, the rotation of the proximal anchor band 46 will not cause any twisting in the central band 20.

Figure 3:
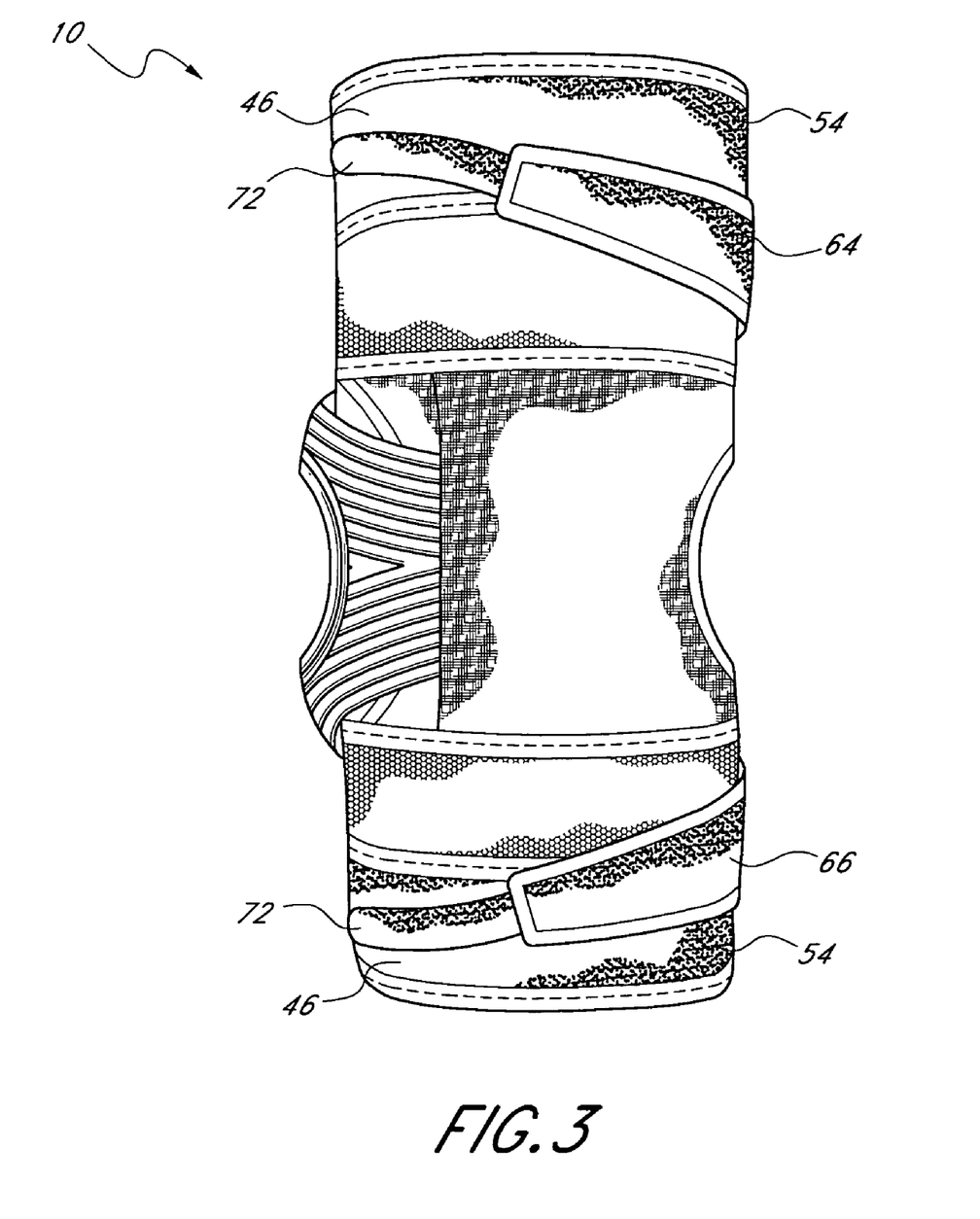
FIG. 3 is a right-side elevational view of the patellofemoral brace of FIG. 1.
Figure 4:
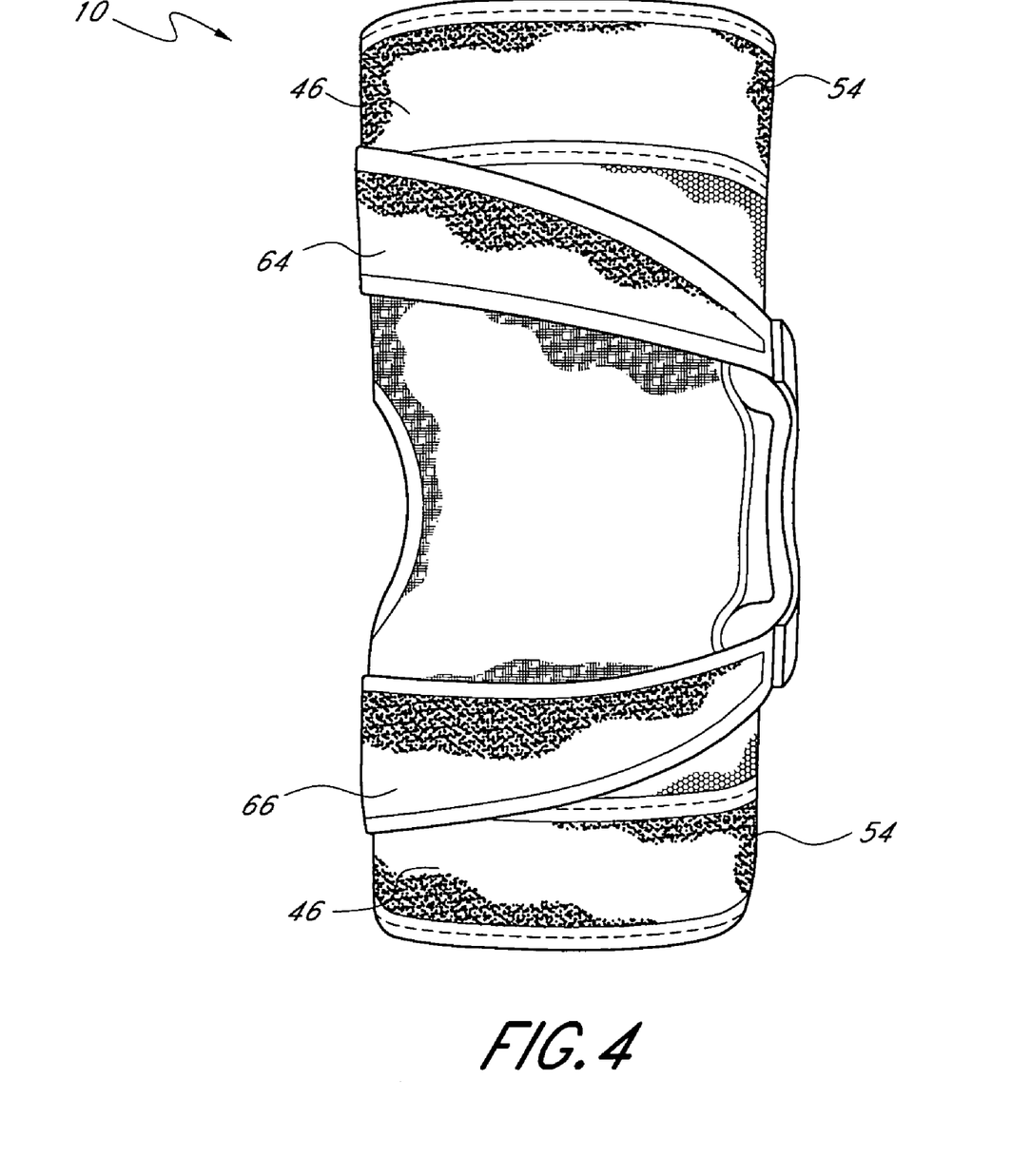
FIG. 4 is a left-side elevational view of the patellofemoral brace of FIG. 1.
Figure 5:
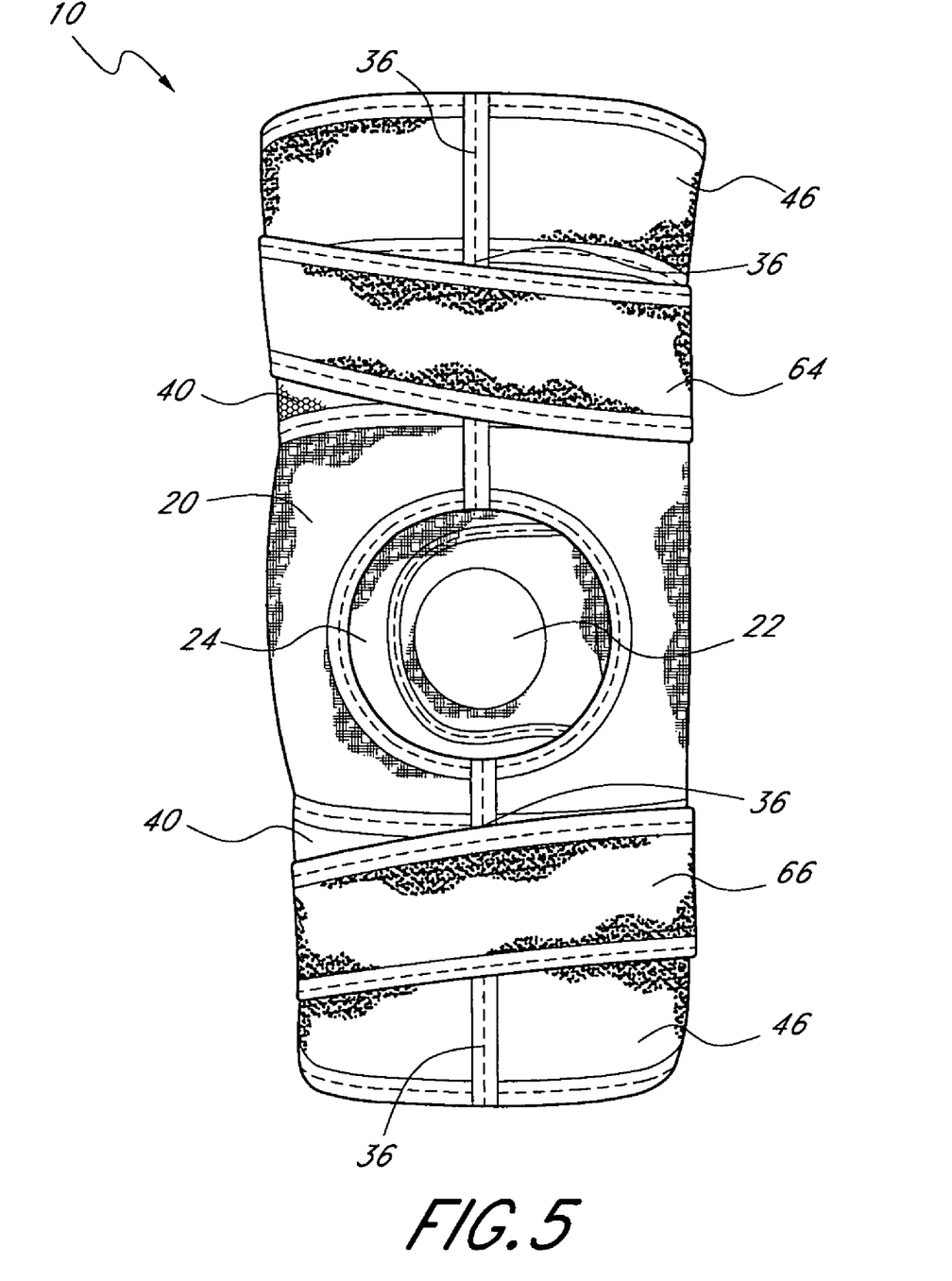
FIG. 5 is a rear elevational view of the patellofemoral brace of FIG. 1.
Figure 6:
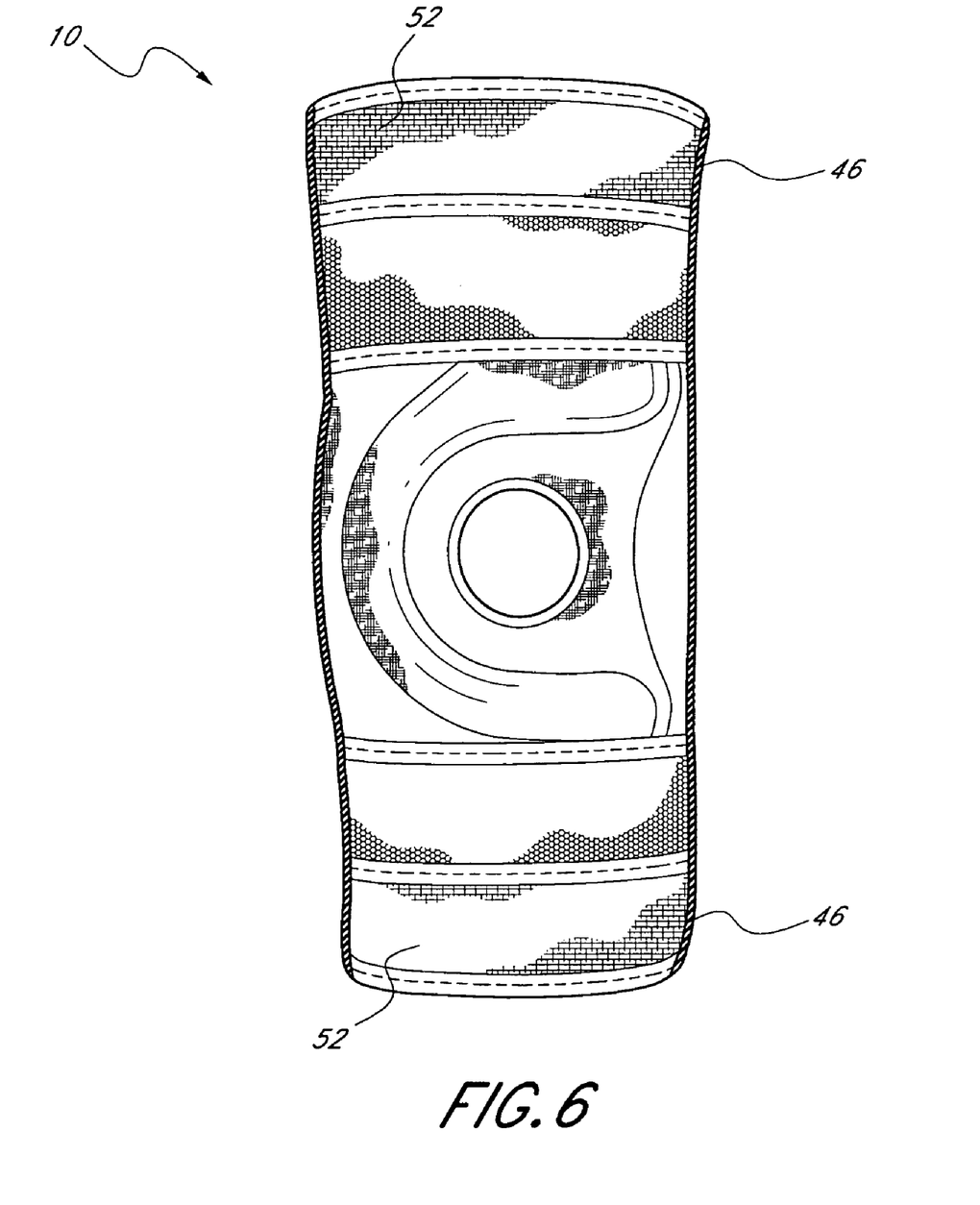
FIG. 6 is a rear sectional view of the patellofemoral brace of FIG. 1, illustrating the inside surface of the anterior portion of the brace.

An inner surface 52 of each anchor band 46 preferably has a high friction coefficient (FIG. 6). For example, the anchor bands 46 may be constructed of single-sided neoprene, or the inner surface 52 of each anchor band 46 may comprise a rubberized material, or the inner surface 52 of each anchor band 46 may be silk-screened with high friction silicone dots. The inner surfaces 52 of the anchor bands 46 thus resist any tendency of the brace 10 to slide up or down the wearer's leg. The inner surfaces 52 of the anchor bands 46 also resist any tendency of the anchor bands 46 to rotate about the wearer's leg. An outer surface 54 of each anchor band 46 preferably comprises a loop portion of a hook-and-loop fastener (FIGS. 3 and 4). The outer surfaces 54 of the anchor bands 46 provide attachment points for ends of the tensioning strap 14, as described below.

The tensioning strap 14 extends from a lateral portion of the central band 20 (FIG. 2). The tensioning strap 14 comprises a substantially V-shaped base portion 56 (FIGS. 1 and 2). The base portion 56 is preferably constructed of a flexible thermoplastic elastomer. The thermoplastic elastomer is preferably thicker and less stretchable than the material used to construct the bands 20, 40, 46 of the sleeve 12. Preferred thermoplastic elastomer include thermoplastic urethane and thermoplastic silicone. The base portion 56 could also be constructed of various naturally occurring materials having the desired properties of flexibility and stretchability, such as rubber. For simplicity, the term thermoplastic elastomer will be used throughout to describe the base portion 56, even though the base portion 56 could be constructed from non-thermoplastic materials.

A base 58 of the V 56 is secured to the lateral portion of the central band 20, preferably with stitching 36. The V 56 extends across the anterior portion of the central band 20, such that the base 58 of the V 56 overlies the rounded base of the buttress 38 (FIG. 1). A proximal branch 60 of the V 56 overlies the proximal portion of the buttress 38, and a distal branch 62 of the V 56 overlies the distal portion of the buttress 38 (FIG. 1). The proximal and distal branches 60, 62 preferably do not cover the anterior opening 22 in the central band 20.

A proximal elongate arm 64 is secured to and extends from an end of the proximal V branch 60 (FIGS. 1 and 2). A distal elongate arm 66 is secured to and extends from an end of the distal V branch 62. The arms 64, 66 are preferably constructed of a flexible fabric, and are preferably secured to the V branches 60, 62 with stitching 36. The arms 64, 66 preferably have a low friction inner surface 68 and a loop portion of a hook-and-loop fastener on an outer surface 70 (FIG. 2). For example, the arms 64, 66 may be constructed of double-sided neoprene with a low-friction material on the inner surface 68, such as nylon or lycra. Alternatively, the arms 64, 66 may be constructed of single-sided neoprene. In the illustrated embodiment, the arms 64, 66 are constructed of the same material as the anchor bands 46. However, those of skill in the art will appreciate that the arms 64, 66 need not be constructed of the same material as the anchor bands 46.

The arms 64, 66 are adapted to wrap around the sleeve 12, as shown in FIGS. 1, 3, 4 and 5. The proximal arm 64 spirals around the proximal spacer band 40, and is securable to the proximal anchor band 46, as shown in FIGS. 1 and 3. The distal arm spirals around the distal spacer band 40, and is securable to the distal anchor band 46, as shown in FIGS. 1 and 3. Ends 72 of the arms 64, 66 preferably include a hook portion of a hook-and-loop fastener on an inner surface 74 thereof (FIG. 2). The ends 72 are thus securable to the outer surfaces 54 of the anchor bands 46, which preferably comprise a loop portion of a hook-and-loop fastener. Those of skill in the art will appreciate that other fasteners, such as snaps or buttons, could be used to secure the ends 72 to the anchor bands 46.

To apply the brace 10 to his or her left knee, a wearer grasps the proximal anchor band 46 and pulls the sleeve 12 over his or her left foot and upward along his or her leg until the central band 20 is disposed about his or her knee. The wearer's patella should be centered within, and protrude slightly from, the aperture 22 in the anterior portion of the central band 20. The proximal anchor band 46 should encircle the wearer's thigh, and the distal anchor band 46 should encircle the wearer's calf.

With the sleeve 12 properly positioned about the wearer's knee, the wearer then grasps the arms 64, 66 of the tension strap 14 and wraps each one around his or her leg. The proximal arm 64 spirals around the proximal spacer band 40 and attaches to the proximal anchor band 46, as shown in FIGS. 1 and 3. The distal arm 66 spirals around the distal spacer band 40 and attaches to the distal anchor band 46, as shown in FIGS. 1 and 3. The wearer pulls each arm 64, 66 an appropriate amount to create a desired amount of tension in the strap 14. Tension in the arms 64, 66 creates tension in the base portion 56, which applies force to the buttress 38 in the posterior and medial directions. The base portion 56 thereby reinforces the patellar support provided by the buttress 38.

The relatively thick thermoplastic elastomer base portion 56 that overlies the buttress 38 provides firmer support than a relatively elastic fabric. In prior art braces, the buttress is enclosed in a fabric, and the entire strap, if one is provided, is constructed of fabric, as described above. These fabrics are generally flexible and flimsy, and thus tend to give more in response to loads applied by the buttress. Thus, when the wearer flexes his or her knee, and his or her patella subluxes, the flimsy material supporting the buttress may not provide adequate support to maintain the buttress in place. If the buttress shifts, then it cannot provide adequate support to the wearer's patella. The firmer material of the thermoplastic elastomer base 56 provides the firmer support necessary to prevent the buttress 38 from shifting when the wearer bends his or her knee.

Furthermore, the thermoplastic elastomer base portion 56 provides more even pressure to the buttress 38 than an inelastic plastic material. For example, the brace manufactured by Breg, Inc., which is described above, includes an inelastic plastic reinforcing member that applies pressure to the buttress. The inelasticity of this member causes it to apply uneven pressure to the buttress, and to fail to provide any "give" in response to the wearer's movements. The uneven pressure distribution creates localized areas of high pressure on the wearer's knee, leading to discomfort for the wearer. The thermoplastic elastomer base portion 56 of the present brace 10 eliminates these areas of high pressure, and provides a more comfortable feel for the wearer.

The ends 72 of the arms 64, 66 are secured to the anchor bands 46, which to some extent are freely rotatable with respect to the central band 20. Thus, tension in the arms 64, 66 tends to pull the anchor bands 46 and rotate them counter-clockwise (as viewed from above). However, friction between the high friction inner surfaces 52 (FIG. 6) of the anchor bands 46 and the wearer's leg resists this rotation. Thus, the anchor bands 46 maintain tension in the strap 14. Tension in the strap 14 in turn maintains pressure on the buttress 38, and the buttress 38 provides support to the patella.

Securing the arms 64, 66 to the substantially rotationally independent anchor bands 46, rather than to the strap 14 itself or to the central band 20, prevents the strap 14 from applying a counterproductive force to the central band 20. Because the central band 20 is insulated from the influence of the arm ends 72, the central band 20 tends not to rotate in an undesired direction, which would remove pressure from the buttress 38. A lack of insulating the buttress from the twisting influence of the arms is a problem present in some prior art braces, as described above.

Furthermore, the rotational independence of the anchor bands 46 allows the anchor bands 46 to rotate about the wearer's leg without affecting the position of the central band 20 or the position of the buttress 38. Thus, as the wearer moves about, any twisting of the anchor bands 46 will not undermine the patellar support provided by the buttress 38.

Integrating the anchor bands 46 with the central band 20 creates a sleeve 12 that is easy to apply to the wearer's leg. The wearer just grasps the sleeve 12 and pulls it up over his or her knee, as described above. The brace 10 is thus far less cumbersome than the brace disclosed in U.S. Pat. No. 5,873,848 to Fulkerson, which is described above.

Figure 7:
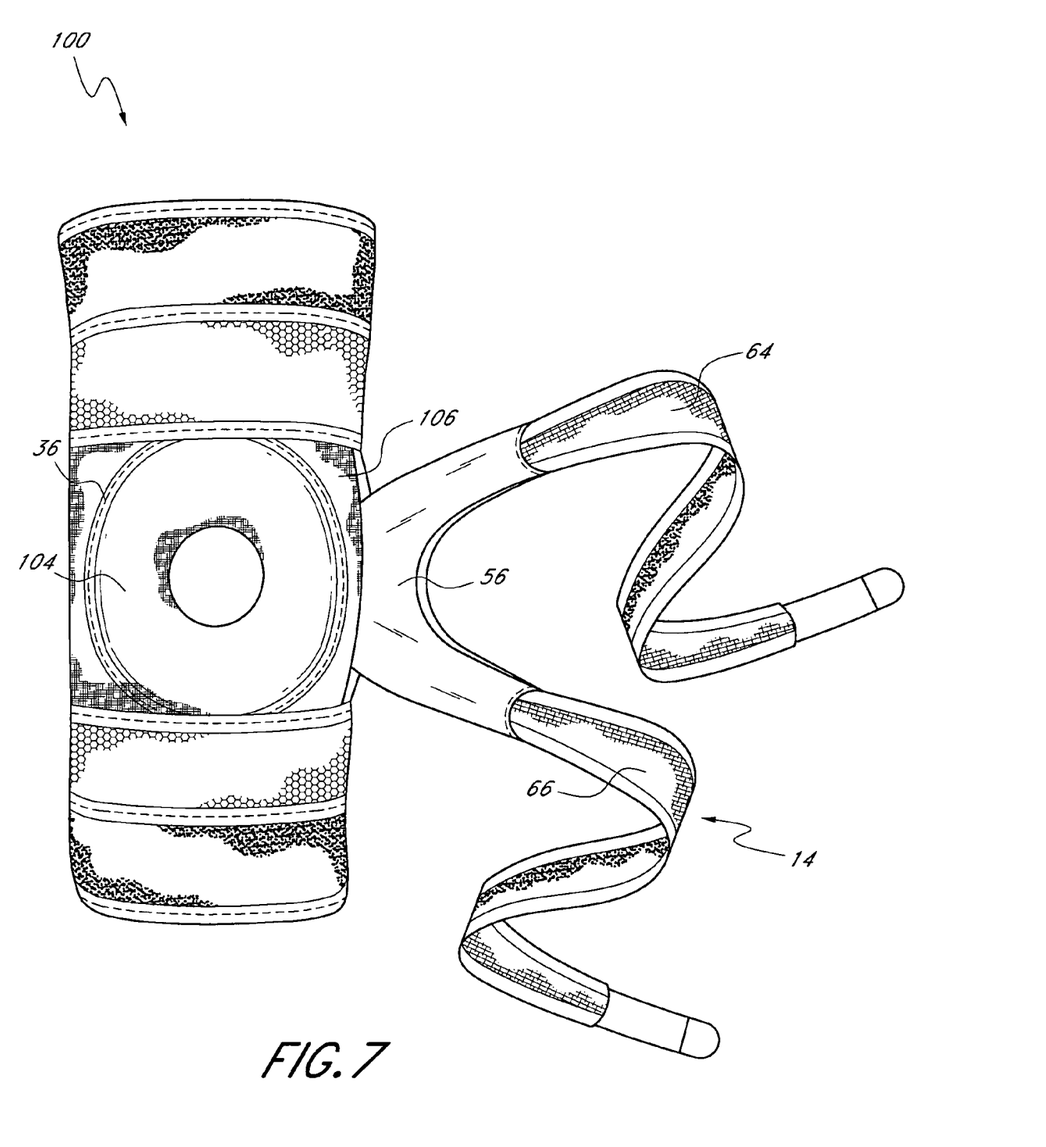
FIG. 7 is a front elevational view of another preferred embodiment of the present patellofemoral brace, illustrating the tensioning strap released from the sleeve.
Figure 8:
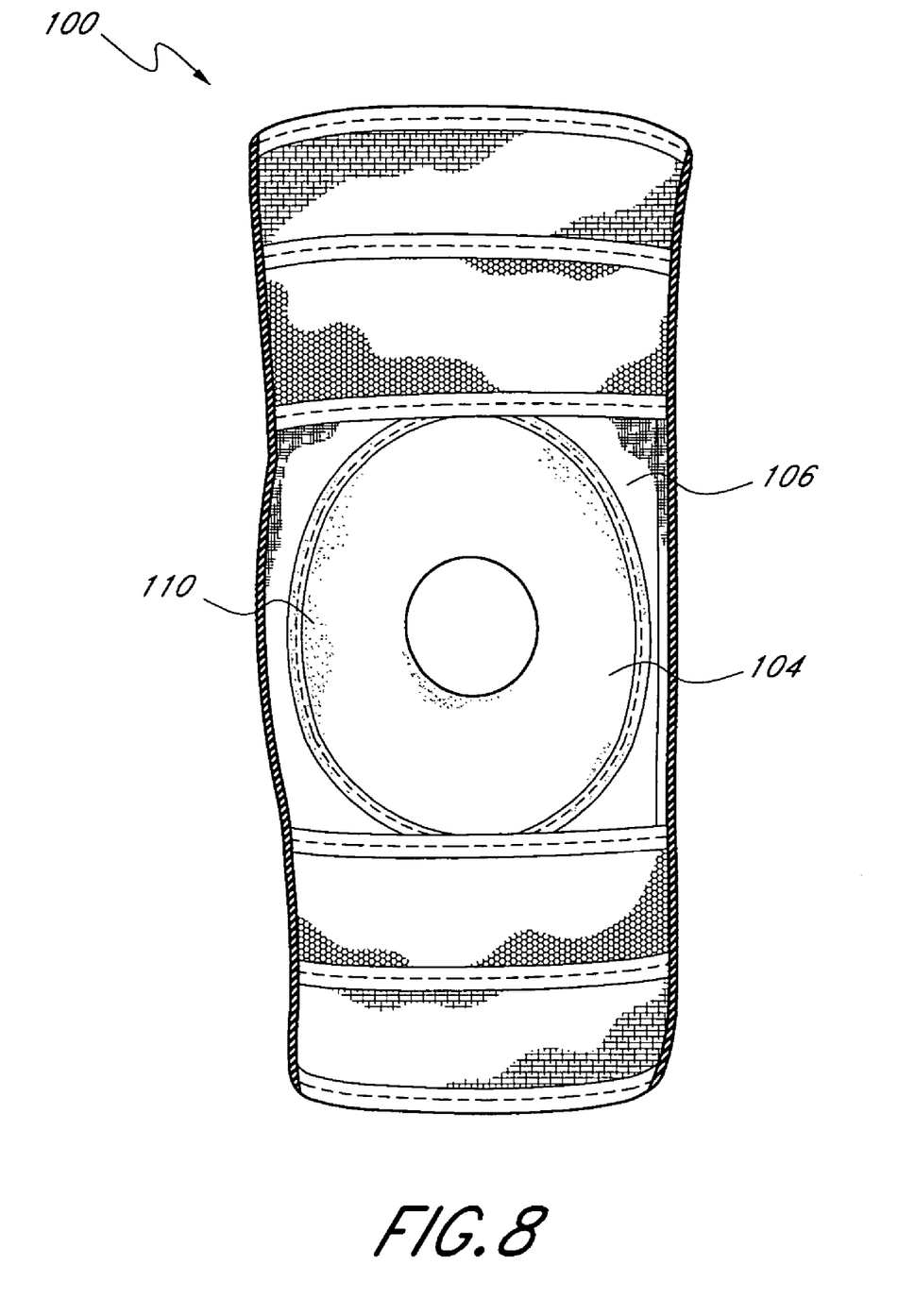
FIG. 8 is a rear sectional view of the patellofemoral brace of FIG. 7, illustrating the inside surface of the anterior portion of the brace.

FIGS. 7-10 illustrate another preferred embodiment of the present patellofemoral brace 100. The brace 100 performs the same functions as the brace 10 described above, and is substantially identical to the brace 10. However, the brace 100 includes a buttress 102 (FIG. 9) that is not sewn into the panel 104 on the central band 106 (FIGS. 7 and 8). Furthermore, the panel 104 is substantially donut shaped, rather than shaped as described above with respect to the brace 10. Those of skill in the art will appreciate that the panel 104 could be virtually any shape. The panel 104 is preferably secured to the central band 106 with stitching 36 (FIG. 7), but the panel 104 could be secured to the central band 106 with other types of fasteners or connecting means such as RF welding.

Figure 9:
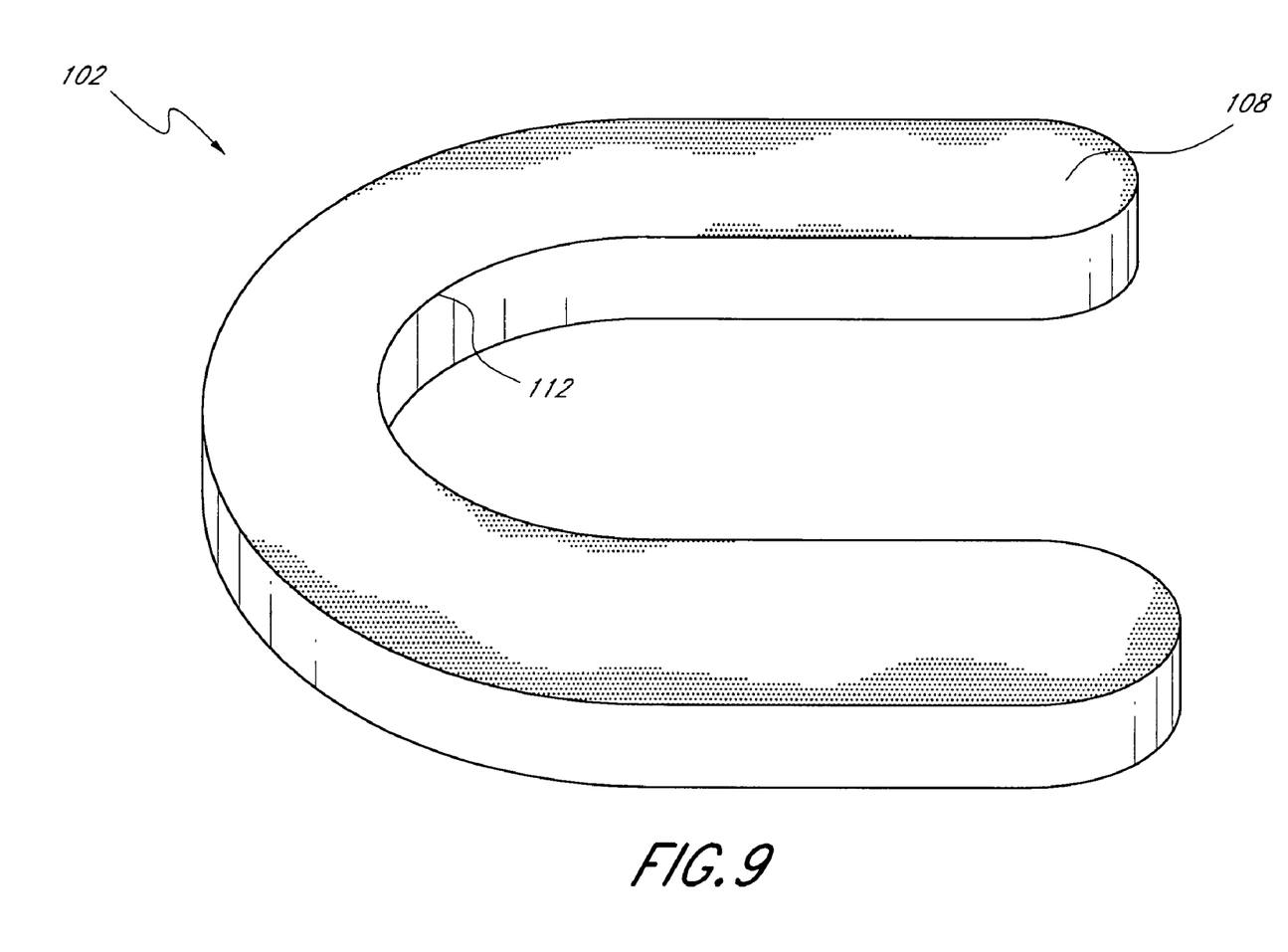
FIG. 9 is a perspective view of a preferred embodiment of the buttress for use with the patellofemoral brace of FIG. 7.
Figure 10:
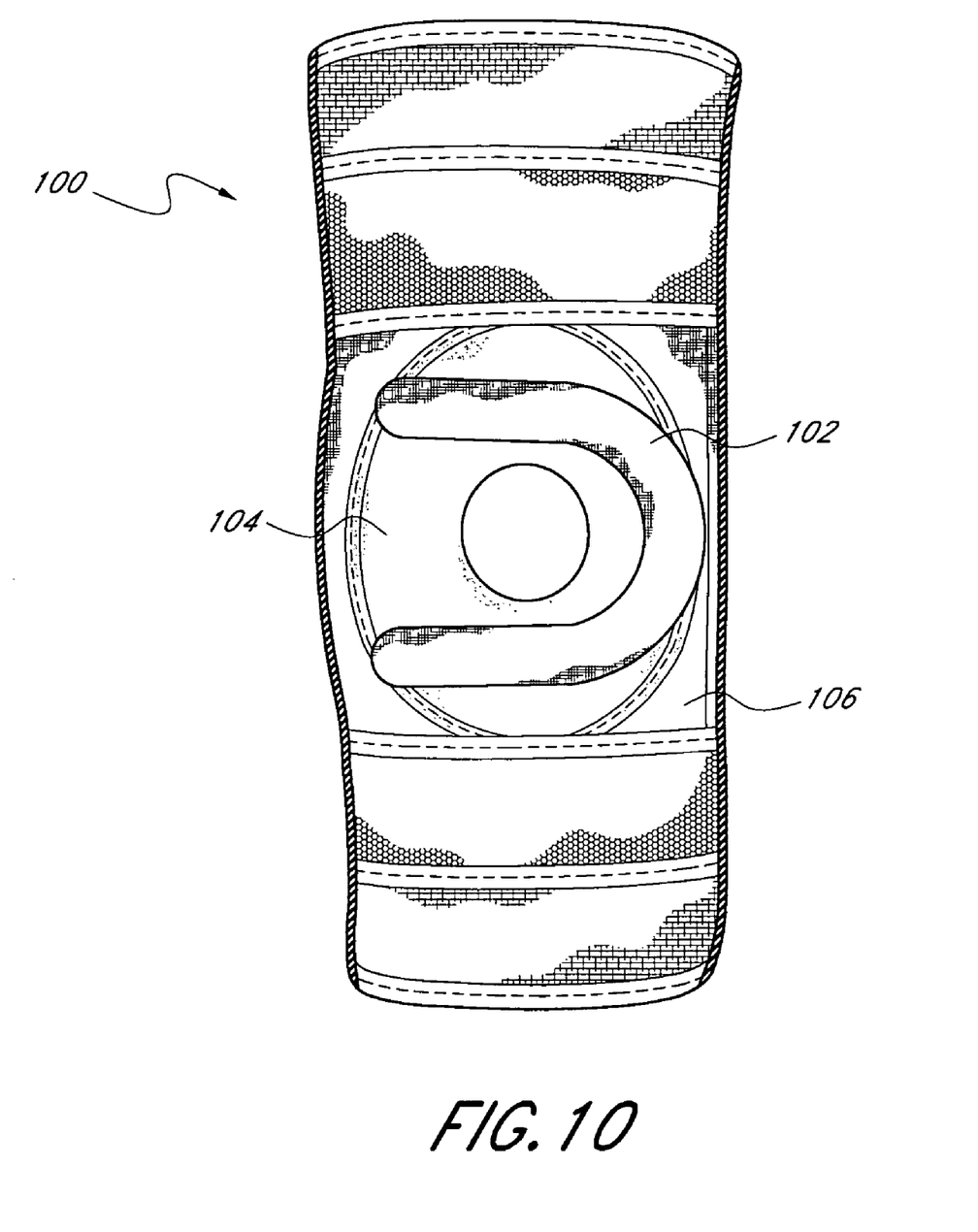
FIG. 10 is a rear sectional view of the patellofemoral brace of FIG. 7, illustrating the buttress of FIG. 9 in position on the brace.

The buttress 102, illustrated in FIG. 9, comprises a C-shaped piece of dense material. Preferred materials for the buttress 102 include those materials recited above for the buttress 38, and also medium density foam and other materials having similar properties. On at least one surface 108, the buttress 102 preferably includes a hook portion of a hook-and-loop fastener. An inner surface 110 (FIGS. 8 and 10) of the panel 104 preferably includes a loop portion of a hook-and-loop fastener. The buttress 102 is thus releasably securable to the inner surface 110 of the panel 104, as shown in FIG. 10. Those of skill in the art will appreciate that the loop portion of a hook-and-loop fastener could be secured to the buttress 102, and the hook portion of a hook-and-loop fastener could be secured to the inner surface 110. Those of skill in the art will further appreciate that the buttress 102 could be secured to the inner surface 110 with other fasteners, such as snaps.

Advantageously, the buttress 102 can be removed and resecured to the inner surface 110. Thus, the buttress 102 can be oriented in whatever fashion is best suited to meet the patellar support needs of a particular patient. Furthermore, a buttress 102 having a particular thickness can be readily exchanged for one of a multitude of other buttresses 102 having different thicknesses. The buttress 102 could also be exchanged for a buttress 102 having a variable, or tapering, thickness. Thus, a manufacturer can produce one brace 100 (in varying sizes, of course) to treat a wide variety of patients, rather than having to produce specially designed braces to treat various forms of patellar subluxation.

Advantageously, the buttress 102 abuts the wearer's patella directly, rather than through the panel 110 material. Preferably, the buttress 102 includes a right-angled edge 112 (FIG. 9). The edge 112 provides a secure grip on the wearer's patella. However, because of the compressibility of the material used to construct the buttress 102, the buttress 102 conforms to the wearer's patella and provides a comfortable feel. Those of skill in the art will appreciate that the buttress 102 need not have a right-angled edge 112. For example, the buttress 102 could have a rounded edge.

SCOPE OF THE INVENTION

The above presents a description of the best mode contemplated for carrying out the present patellofemoral brace, and of the manner and process of making and using it, in such full, clear, concise, and exact terms as to enable any person skilled in the art to which it pertains to make and use this patellofemoral brace. This patellofemoral brace is, however, susceptible to modifications and alternate constructions from that discussed above that are fully equivalent. Consequently, this patellofemoral brace is not limited to the particular embodiments disclosed. On the contrary, this patellofemoral brace covers all modifications and alternate constructions coming within the spirit and scope of the patellofemoral brace as generally expressed by the following claims, which particularly point out and distinctly claim the subject matter of the patellofemoral brace.

What is claimed is:

1. A patellofemoral brace for supporting a patella of a wearer's knee, the brace comprising:
    a substantially cylindrical sleeve configured to be worn on a wearer's leg and to extend above and below the wearer's knee, the sleeve subdivided into a plurality of circumferential discrete bands configured to extend around a portion of the wearer's leg, and the sleeve including an aperture on an anterior portion thereof, the aperture configured to encircle the wearer's patella when the brace is worn;
    a buttress cooperating with the sleeve and configured to apply force to the patella when the brace is worn; and
    a tensioning strap cooperating with the sleeve and configured to overlie the buttress to increase the force applied to the patella by the buttress;

wherein the tensioning strap includes a base portion and first and second arms, each of the first and second arms being configured to extend around the sleeve along first and second, respectively, substantially helical paths.

2. The patellofemoral brace of claim 1, wherein the base portion of the tensioning strap is substantially V-shaped.

3. The patellofemoral brace of claim 2, wherein a vertex of the base portion extends from a side of the sleeve, and first and second branches of the base portion are configured to extend across a front of the sleeve above and below the knee, respectively, when the brace is worn.

4. The patellofemoral brace of claim 1, wherein when the arms are wrapped around the sleeve, the base portion overlies the buttress and applies an amount of pressure thereto that varies according to an amount of tension in the strap.

5. The patellofemoral brace of claim 1, wherein the base portion is constructed of at least one of thermoplastic elastomer, thermoplastic urethane, thermoplastic silicone and rubber.

6. The patellofemoral brace of claim 1, wherein the buttress at least partially surrounds the aperture.

7. The patellofemoral brace of claim 1, wherein the buttress comprises an elongate strip of dense material.

8. The patellofemoral brace of claim 7, wherein the buttress comprises at least one of felt, neoprene foam and ethyl-vinyl acetate.

9. The patellofemoral brace of claim 1, wherein at least a portion of an inner surface of the sleeve is constructed of a material that does not slide easily against human skin.

10. The patellofemoral brace of claim 1, wherein the sleeve comprises a central band configured to lie proximate the wearer's knee, a proximal spacer band secured to a proximal edge of the central band, a distal spacer band secured to a distal edge of the central band, a proximal anchor band secured to a proximal edge of the proximal spacer band, and a distal anchor band secured to a distal edge of the distal spacer band.

11. The patellofemoral brace of claim 10, wherein ends of the first and second arms are securable to the proximal and distal anchor bands, respectively.

12. A method of supporting a patella of a wearer's knee, the method comprising the steps of:

applying to the knee a patellofemoral brace, the brace including a substantially cylindrical sleeve extending above and below the wearer's knee, the sleeve subdivided into a plurality of circumferential discrete bands configured to extend around a portion of the wearer's leg, including an anchor band and a central band, and, the sleeve including a buttress cooperating with the sleeve and operatively abutting the patella; and tightening a tensioning strap around the leg such that a base portion of the strap overlies the buttress and applies force thereto, and first and second arms of the strap extend around the sleeve along first and second, respectively, substantially helical paths, and wherein applying the brace to a knee comprises positioning the anchor band about a thigh of the wearer and positioning the central band about the wearer's knee.

13. The method of claim 12, wherein the base portion is constructed of at least one of a thermoplastic elastomer, thermoplastic urethane, thermoplastic silicone and rubber, and the first and second arms are constructed of a flexible fabric.

14. A patellofemoral brace for supporting a patella of a wearer's knee, the brace comprising:

a substantially cylindrical sleeve configured to be worn on a wearer's leg and to extend above and below the wearer's knee, the sleeve subdivided into a plurality of discrete arcuate bands configured to extend around a portion of the wearer's leg, and the sleeve including an aperture on an anterior portion thereof, the aperture configured to encircle the wearer's patella when the brace is worn;

a buttress cooperating with the sleeve and configured to apply force to the patella when the brace is worn; and a tensioning strap cooperating with the sleeve and configured to overlie the buttress to increase the force applied to the patella by the buttress;

wherein the tensioning strap includes a base portion and first and second arms, each of the first and second arms being configured to extend around the sleeve along first and second, respectively, substantially helical paths.

* * * * *